US010174311B2

(12) United States Patent
Felgner et al.

(10) Patent No.: US 10,174,311 B2
(45) Date of Patent: Jan. 8, 2019

(54) COMPOSITIONS AND METHODS FOR IMMUNODOMINANT ANTIGENS

(71) Applicant: ImmPORT Therapeutics, Inc., Irvine, CA (US)

(72) Inventors: Philip Felgner, Rancho Sante Fe, CA (US); David Huw Davies, Long Beach, CA (US); Xiaowu Liang, La Jolla, CA (US)

(73) Assignee: Immport Therapeutics, Inc., Irvine, CA (US)

( * ) Notice: Subject to any disclaimer, the term of this patent is extended or adjusted under 35 U.S.C. 154(b) by 269 days.

(21) Appl. No.: 15/285,421

(22) Filed: Oct. 4, 2016

(65) Prior Publication Data

US 2017/0081659 A1 Mar. 23, 2017

Related U.S. Application Data

(62) Division of application No. 14/518,415, filed on Oct. 20, 2014, which is a division of application No. 12/447,620, filed as application No. PCT/US2007/023299 on Nov. 1, 2007, now Pat. No. 9,297,803.

(60) Provisional application No. 60/856,217, filed on Nov. 1, 2006.

(51) Int. Cl.

| | |
|---|---|
| *C12Q 1/68* | (2018.01) |
| *C12N 15/10* | (2006.01) |
| *A61K 39/015* | (2006.01) |
| *A61K 39/02* | (2006.01) |
| *A61K 39/04* | (2006.01) |
| *A61K 39/118* | (2006.01) |
| *A61K 39/245* | (2006.01) |
| *A61K 39/285* | (2006.01) |
| *A61K 39/385* | (2006.01) |
| *C07K 14/005* | (2006.01) |
| *G01N 33/566* | (2006.01) |
| *A61K 39/12* | (2006.01) |
| *G01N 33/569* | (2006.01) |
| *G01N 33/68* | (2006.01) |
| *A61K 39/00* | (2006.01) |

(52) U.S. Cl.
CPC ........ *C12N 15/1068* (2013.01); *A61K 39/015* (2013.01); *A61K 39/0208* (2013.01); *A61K 39/0225* (2013.01); *A61K 39/04* (2013.01); *A61K 39/098* (2013.01); *A61K 39/118* (2013.01); *A61K 39/12* (2013.01); *A61K 39/245* (2013.01); *A61K 39/285* (2013.01); *A61K 39/385* (2013.01); *C07K 14/005* (2013.01); *G01N 33/566* (2013.01); *G01N 33/5695* (2013.01); *G01N 33/56911* (2013.01); *G01N 33/56916* (2013.01); *G01N 33/56927* (2013.01); *G01N 33/56983* (2013.01); *G01N 33/56994* (2013.01); *G01N 33/6854* (2013.01); *A61K 2039/60* (2013.01); *C12N 2710/16621* (2013.01); *C12N 2710/16622* (2013.01); *C12N 2710/16634* (2013.01); *C12N 2710/24122* (2013.01); *C12N 2710/24134* (2013.01); *G01N 2333/35* (2013.01); *G01N 2469/20* (2013.01); *Y02A 50/401* (2018.01); *Y02A 50/412* (2018.01)

(58) Field of Classification Search
None
See application file for complete search history.

(56) References Cited

PUBLICATIONS

Davies et al. PNAS 102(3):547-552 (Year: 2005).*

* cited by examiner

*Primary Examiner* — Samuel C Woolwine
(74) *Attorney, Agent, or Firm* — Umberg Zipser, LLP

(57) ABSTRACT

Contemplated compositions, devices, and methods comprise immunodominant antigens from selected human pathogens (*Burkholderia pseudomallei, Borrelia burgdorferi, Brucella melitensis, Chlamydia muridarum, Coxiella burnetii, Francisella tularensis*, human Herpes virus 1 and 2, *Mycobacterium tuberculosis, Plasmodium falciparum*, and *Vaccinia virus*) can be used as a vaccine, as diagnostic markers, and as therapeutic agents. In particularly preferred aspects, the antigens have quantified and known relative reactivities with respect to sera of a population infected with the pathogen, and have a known association with a disease parameter.

14 Claims, 4 Drawing Sheets

Specification includes a Sequence Listing.

COMPOSITIONS AND METHODS FOR IMMUNODOMINANT ANTIGENS

This application is a divisional application of U.S. application Ser. No. 14/518,415 filed Oct. 20, 2014, which is a divisional application of U.S. application Ser. No. 12/447,620, filed Dec. 3, 2009, which is a U.S. National Phase filing of International Application No. PCT/US07/23299, filed Nov. 1, 2007, which claims priority to U.S. Provisional Application No. 60/856,217, filed Nov. 1, 2006.

FIELD OF THE INVENTION

The field of the invention is immunodominant antigens from pathogens, especially as they relate to their use in diagnostic and therapeutic compositions and methods.

BACKGROUND OF THE INVENTION

Antigens for vaccination and/or diagnostic purposes are typically single antigens from a pathogen, or complex mixtures of multiple and unknown antigens of a pathogen such as inactivated bacteria or viruses. Depending on the particular type of pathogen, single antigens may provide a quantifiable signal in diagnostic test. However, due to variations among individuals in their immune response profiles, single antigen tests are often not sufficient to obtain useful diagnostic information with useful specificity and sensitivity. In addition, where the single antigen is used as a vaccine, variability of individual immune response and potential prior exposure often limit usefulness of single antigens. Finally, while some complex mixtures of multiple and unknown antigens are useful for vaccine development, they typically carry the risk of adverse reactions, or even reactivation of the pathogen.

More recently, multivalent vaccine preparations have become available where in a single dose, multiple and distinct antigens, from multiple and distinct serotypes, of a single pathogenic organisms were combined (Prevnar™: Heptavalent vaccine against *Streptococcus pneumoniae* capsular serotypes 4, 6B, 9V, 14, 18C, 19F, and 23F). While such mixed preparations tend to provide a broader range of protection against different serotypes, various difficulties nevertheless remain. Most significantly, where a single antigen fails to elicit an immune response, coverage to the corresponding serotype is not present. Thus, combination of single defined antigens from several serotypes merely combines benefits and problems associated with the single antigens. Moreover, none of the heretofore known antigens is generally applicable to differentiate among stages, secondary infections, etc., as the signal is either impossible to deconvolute (e.g., compound signal from inactivated pathogen) or only provides a single data point.

Therefore, while numerous methods of identification and use of antigens are known in the art, all or almost all of them suffer from one or more disadvantages. Consequently, there remains a large, unmet need to provide improved compositions and methods of antigens for diagnostic and therapy.

SUMMARY OF THE INVENTION

The present invention is directed to immunodominant antigens from various human pathogens wherein the antigens have predetermined reactivities to serum of a population of patients infected with the pathogen. Thus, immunodominant antigens will have a statistically high probability to elicit an immune response in a relatively large group of patients. Further, where the antigens are determined from selected sub-populations (e.g., primary infection, secondary infection, recovering, chronic etc.), the antigens also have a known association with a disease parameter.

In one aspect of the inventive subject matter, an antigen composition comprises two or more immunodominant antigens of a pathogenic organism and are associated with a carrier, wherein the antigens have quantified and known relative reactivities with respect to sera of a population infected with the organism, and wherein the antigens have a known association with a disease parameter. Most preferably, the antigens are polypeptides and are encoded by nucleic acids having a sequence according to SEQ ID NO:1 to SEQ ID NO:1150 (or comprise fragments thereof).

Thus, in some aspects, the pathogenic organism is *Burkholderia pseudomallei*, and the antigens are encoded by nucleic acids having a sequence according to SEQ ID NO:966 to SEQ ID NO:1150, or the pathogenic organism is *Borrelia burgdorferi*, and the antigens are encoded by nucleic acids having a sequence according to SEQ ID NO:546 to SEQ ID NO:637. In further aspects, the pathogenic organism is *Chlamydia muridarum*, and the antigens are encoded by nucleic acids having a sequence according to SEQ ID NO:1 to SEQ ID NO:134, or the pathogenic organism is *Coxiella burneti*, and the antigens are encoded by nucleic acids having a sequence according to SEQ ID NO:678 to SEQ ID NO:713. In yet further aspects, the pathogenic organism is *Francisella tulare*, and the antigens are encoded by nucleic acids having a sequence according to SEQ ID NO:663 to SEQ ID NO:677, or the pathogenic organism is human Herpes virus 1, and the antigens are encoded by nucleic acids having a sequence according to SEQ ID NO:638 to SEQ ID NO:654, or the pathogenic organism is human Herpes virus 2, and the antigens are encoded by nucleic acids having a sequence according to SEQ ID NO:655 to SEQ ID NO:662. In still further aspects, the pathogenic organism is *Mycobacterium tuberculosis*, and the antigens are encoded by nucleic acids having a sequence according to SEQ ID NO:749 to SEQ ID NO:965, or the pathogenic organism is *Plasmodium falciparum*, and the antigens are encoded by nucleic acids having a sequence according to SEQ ID NO:135 to SEQ ID NO:445. In yet further aspects, the pathogenic organism is *Brucella melitensis*, and the antigens are encoded by nucleic acids having a sequence according to SEQ ID NO:446 to SEQ ID NO:545, or the pathogenic organism is *Vaccinia virus*, and the antigens are encoded by nucleic acids having a sequence according to SEQ ID NO:714 to SEQ ID NO:748.

It is further contemplated that the known reactivities may be characterized by a variety of factors, however, it is particularly preferred that the known reactivities are characterized by strength of immunogenicity and/or time course of the infection. Similarly, the particular parameter may vary among different pathogens, however, it is generally preferred that the parameter is a previous exposure to the pathogen, the duration of exposure to the pathogen, a chronic infection, at least partial immunity to infection with the pathogen, and/or an expected positive outcome upon treatment.

In another aspect of the inventive subject matter, the carrier is a pharmaceutically acceptable carrier, and the composition is formulated as a vaccine. In such aspects, it is generally preferred that the vaccine comprises multiple (e.g., at least two, four, or six) antigens, which may be from the same pathogen or distinct (serotypical or species) pathogens.

Depending on the particular pathogen, it is contemplated that the antigens or fragments thereof are at least partially purified and/or recombinant.

Alternatively, the carrier may also be a solid carrier, and the plurality of antigens is disposed on the carrier in an array. In such arrays, it is generally preferred that the antigens are from at least two distinct pathogens, and/or have at least two distinct known reactivities and/or parameters. It is further contemplated that the antigens or fragments thereof may be in crude expression extracts, in partially purified form (e.g., purity of less than 60%), or in highly purified form (purity of at least 95%). The antigens in such arrays may be recombinant or native. Alternatively, solid phases need not be limited to planar arrays, but may also include beads, columns, dipstick-type formats, etc.

Various objects, features, aspects and advantages of the present invention will become more apparent from the following detailed description of preferred embodiments of the invention.

DETAILED DESCRIPTION

Figure 1:
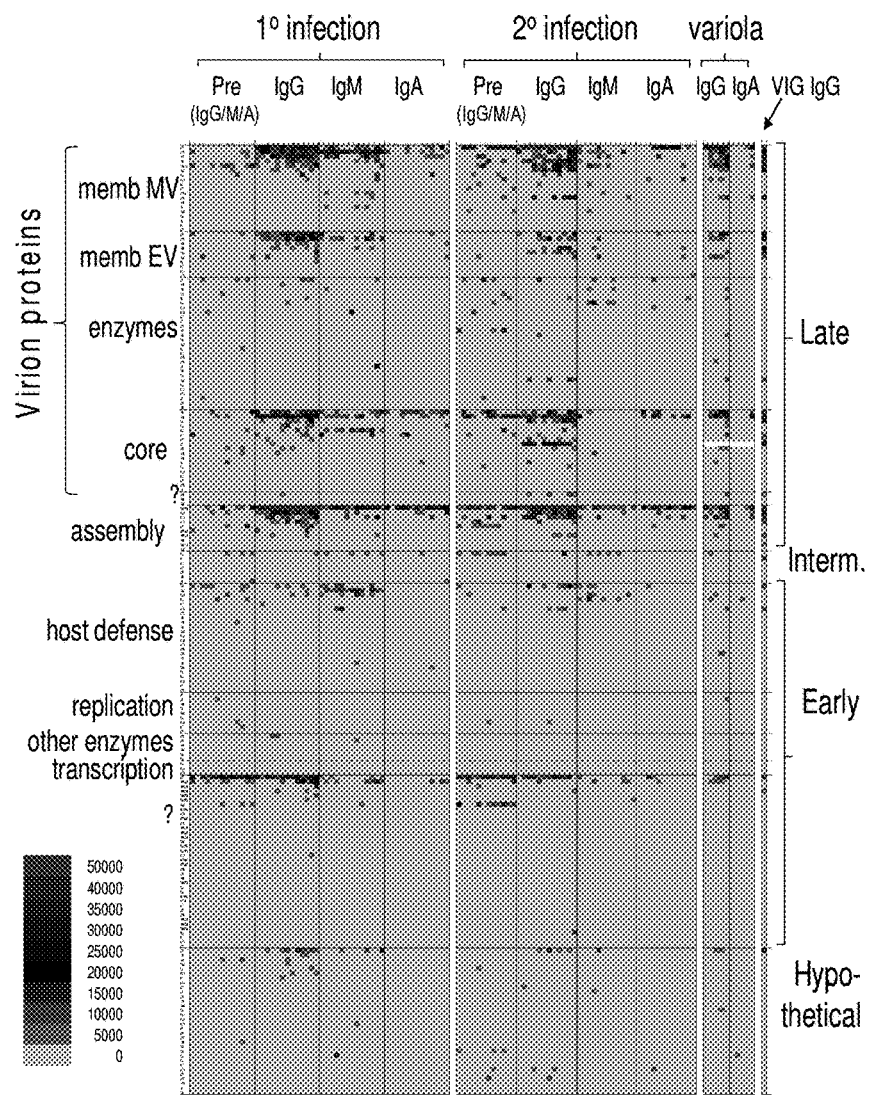
FIG. 1 is an exemplary matrix depicting antibody signals for selected antibody types with respect to potential antigens of an exemplary pathogen.

The inventors have discovered numerous immunodominant antigens from a variety of human pathogens capable of casing infection in humans, including: *Burkholderia pseudomallei*, *Borrelia burgdorferi*, *Brucella melitensis*, *Chlamydia muridarum*, *Coxiella burnetii*, *Francisella tularensis*, human Herpes virus 1 and 2, *Mycobacterium tuberculosis*, *Plasmodium falciparum*, and *Vaccinia virus*. Immunodominant antigens according to the inventive subject matter are encoded by nucleic acids having a sequence according to SEQ ID NO:1 to SEQ ID NO:1150, and it is generally contemplated that such antigens can be used by themselves, or more preferably, in combination with other antigens (typically also immunodominant antigens) in the manufacture of a diagnostic devices, therapeutic compositions, and vaccines.

As used herein, the term "immunodominant antigen" refers to an antigen that elicits in at least one stage of the disease production of one or more types of antibodies (e.g., IgG, IgA, IgE, IgM, etc.) in at least 40%, more typically at least 70%, and most typically at least 90% of a population exposed to the antigen, and wherein, when compared to other antigens of the same pathogen, the average binding affinity and/or average quantity of the antibodies produced in the patient in at least one stage of the disease is at least in the upper tertile, more typically upper quartile, and most typically upper quintile. Most typically, the average binding affinity and/or average quantity of the antibodies is reflected in the signal intensity and signal intensity can therefore be used as a surrogate marker for average binding affinity and/or average quantity of the antibodies. In further aspects, preferred immunodominant antigens are also characterized by a response in the test group that is considered statistically significant when compared with control signal intensity, wherein the significance level p is preferably equal or less than 0.1, more preferably equal or less than 0.05, and most preferably equal or less than 0.01.

In one aspect of the inventive subject matter, immunodominant antigens are identified from a proteome screen against sera of a population that has been previously exposed to the pathogen. Most preferably, the population is subdivided in several sub-populations to reflect various disease parameters, which can then be correlated with the so identified antigens. It is still further preferred that the screening also provides data on relative reactivities with respect to the antigens and sera of the populations/sub-populations.

With respect to the above pathogens, it is generally preferred that at least part of the pathogen's genome is obtained and all potential open reading frames and splice mutations thereof are determined in silico. Once the potential genes are identified, suitable primers are determined to provide amplicons of the entire Open Reading Frames (ORFs), or, less preferably, portions thereof, wherein the primers are preferably designed to allow facile subcloning into an expression system. Most preferably, the subcloning uses recombinase-based subcloning using unpurified PCR mixtures to avoid cloning bias, and the so obtained recombinant plasmids are polyclonally multiplied, which enables unbiased presentation of the amplicons. It is still further particularly preferred that the plasmid preparations are then subjected to an in vitro transcription/translation reaction to thereby provide the recombinant ORF peptide, which is then spotted or otherwise immobilized onto a suitable addressable carrier (e.g., membrane, bead, etc.).

It should be recognized that the so prepared proteomes can then be exposed to serum of a population of control individuals and/or population of individuals that are known to have current or previous exposure to the above pathogen from which the ORFs were prepared. Antibodies of the serum that bind to one or more of the ORFs are then detected using well known methods (e.g., secondary antibodies). In this manner, the entire proteome of the pathogen can be rapidly assessed for immunogenicity and potential binding with antibodies in serum. Various preferred aspects, compositions, and methods of proteome preparation are disclosed in our International patent application with the publication number WO 06/088492, which is incorporated by reference herein.

Therefore, and among various other advantages, it should be especially recognized that contemplated compositions and methods presented herein will allow for preparation of vaccines and diagnostic compositions comprising a plurality of antigens with known and predetermined affinity to target ORFs of a pathogen. As individual immune systems are known to exhibit significant variation with respect to antigen recognition, methods and compositions contemplated herein will allow statistically supported antigen identification to identify immunodominant antigens in a population of patient. Consequently, multiple targets can be used to elicit an immune response and/or detect a prior exposure, even where one or more of the targets may be evasive for detection or provide only a weak response.

With respect to the immunodominant sequences identified herein, it should be further appreciated that the sequences need not be complete ORFs, but that suitable sequences may also be partial sequences (e.g., synthetic, recombinant or isolated) that typically comprise at least part of an antigenic epitope. Thus, sequences contemplated herein may be identified as DNA sequences encoding the antigenic peptide (partial or entire ORF), or may be identified as peptide sequence (or homologs thereof). Similarly, chemically modified antigens, and/or orthologs of the polypeptides presented herein are also deemed suitable for use herein.

It should be particularly noted that while proteome screening will provide a plurality of antigens as potentially useful molecules for diagnosis, vaccination, and/or therapy, such an approach only provides a raw cut of (a plurality) of individual responses. Thus, as most individual immune reactions towards the same pathogen elicit a significantly distinct profile of antibodies (e.g., depending on disease stage, previous exposure, and/or inter-individual variability), results obtained from such screening are typically inhomogeneous. Consequently, variability of the individual immune responses and variability of the quantity of recombinant protein in the array must be taken into consideration to obtain meaningful results.

Therefore, it should be appreciated that filtering of raw data will result in a collection of antigens with quantified and known relative reactivities with respect to sera of a population infected with the pathogen. Moreover, it should be noted that as signals may be specific to a particular stage in the course of an infection, relative reactivities may be indicative of the time course of the infection, and/or relative reactivities may represent differences in the strength of immunogenicity of the particular antigen (or quantity of deposited antigen in the screening assay). Additionally, it should be particularly recognized that depending on the choice of the specific patient population, the tested sera will reflect the immune status of a population that is characterized by one or more parameters of the disease. For example, populations may be observed that are infected or not infected, that had a long-term exposure or chronic infection, that had spontaneous recovery, that represents a group of responders (or non-responders) to a particular drug treatment, or that had at least partial immunity to the pathogen.

In still further contemplated aspects, immunodominant antigens are identified by selecting for an antigen (preferably within a well-defined sub-population) that (a) produces in at least 40-50% of a population a measurable signal, and (b) has a signal strength of at least 40% of the overall average signal intensity. However, and more preferably, the signal strength will be at least above average of the overall average signal intensity, and even more preferably in the upper tertile (quartile, or even quintile) of signal intensities in the assay. Therefore, and viewed from another perspective, immunodominant antigens will preferably be selected in a comparison of at least two series of tests, wherein one series of tests is typically the sub-population (e.g., primary infection, secondary infection, recovering, chronic, etc.) and the other series of tests is the control group (e.g., other sub-population or control group). Still further, it is generally preferred that the series of tests also include a negative control against which the potential immunodominant antigens are compared.

Consequently, and with particular respect to the pathogens presented herein, it should be appreciated that compositions comprising one or more selected immunodominant antigens can be prepared that will have a statistically high probability to elicit or have elicited an immune response in a relatively large group of patients. Further, where the antigens are determined from selected sub-populations (e.g., recovering patients, chronic patients, primary infection, secondary infection, etc.), the antigens also have a known association with a disease parameter and thus allow staging of the disease and/or prediction of therapeutic efficacy. Moreover, as the antigens presented herein are immunodominant antigens, it should be noted that vaccine compositions can be prepared with known or predictable immunogenicity.

For example, numerous antigens of *Burkholderia pseudomallei* (those encoded by nucleic acids SEQ ID NO:966 to SEQ ID NO:1150), *Borrelia burgdorferi* (those encoded by nucleic acids SEQ ID NO:546 to SEQ ID NO:637), *Chlamydia muridarum* (those encoded by nucleic acids SEQ ID NO:1 to SEQ ID NO:134), *Coxiella burnetii* (those encoded by nucleic acids SEQ ID NO:678 to SEQ ID NO:713), *Francisella tularensis* (those encoded by nucleic acids SEQ ID NO:663 to SEQ ID NO:677), Herpes virus 1, Herpes virus 2, and *Vaccinia virus* (those encoded by nucleic acids SEQ ID NO:638 to SEQ ID NO:654, SEQ ID NO:655 to SEQ ID NO:662, and SEQ ID NO:714 to SEQ ID NO:748, respectively), *Mycobacterium tuberculosis* (those encoded by nucleic acids SEQ ID NO:749 to SEQ ID NO:965), *Plasmodium falciparum* (those encoded by nucleic acids SEQ ID NO:135 to SEQ ID NO:445), and *Brucella melitensis* (those encoded by nucleic acids SEQ ID NO:446 to SEQ ID NO:545) were identified as immunodominant (see also examples and protocol below). With respect to the reading frame for each of the sequences of SEQ ID NO:1 to SEQ ID NO:1150, it should be noted that the first base in the sequences is either the first base of the start codon or the first base in the first codon of the polypeptide that was identified with the methods and compositions provided herein. Most typically, the last three bases denote the stop codon, or the last base of the last codon of the polypeptide that was identified with the methods and compositions provided herein.

In these examples, each of the antigens was characterized, inter alia, with regard to their individual and relative reactivities for each of the pathogens. Most typically, reactivity was measured as strength of immunogenicity (e.g., such that average binding affinity and/or average quantity of the antibodies produced a predetermined signal intensity (e.g., in the upper half, upper tertile, or even upper quartile)). Furthermore, each of the identified antigens was also characterized by association with at least one parameter. In most cases, the disease parameter was acute infection with the pathogen, and in further cases, the disease parameter was also primary and/or secondary infection. Therefore, it should be especially appreciated that identification of immunodominant antigens will not only allow for identification of statistically meaningful antigens for diagnosis, vaccine development, and treatment, but also allow to develop a stage and disease specific tool to identify candidate molecules to fine-tune diagnosis and/or treatment.

For example, suitable diagnostic devices especially include those comprising one or more of the immunodominant antigens, fragments, or analogs thereof that are encoded by nucleic acids according to SEQ ID NO:1 to SEQ ID NO:1150. Depending on the particular device format, the device may have only a single immunodominant antigen, fragment, or analog that may be used for detection of binding of antibodies from blood or serum in an automated manner or by visual observation. For example, where a single immunodominant antigen is employed, suitable devices may be in the format of a dipstick or competitive ELISA. On the other hand, where multiple immunodominant antigens are employed, suitable devices may be in the format of an array that can be read in an automated device (e.g., via scanner) or visual manner (e.g., dye-forming colorimetric reaction). Most typically, in such devices, the plurality of antigens is deposited in a spatially addressable manner (e.g., x-y matrix or mixed beads with color association). Moreover, it should be noted that diagnostic devices contemplated herein may be based on numerous well known manners of detection, including ELISA (sandwich or non-sandwich), competitive ELISA, anti-idiotypic antibodies, etc., wherein all known colorimetric and photometric (e.g., fluorescence, luminescence, etc.) or radiometric reactions are deemed suitable for use.

In most typical devices, a plurality of immunodominant antigens of a single (or multiple) pathogen and/or serotype are deposited onto an addressable solid phase and exposed to blood, serum, plasma or other antibody-containing body fluid. Consequently, so prepared compositions can be employed to identify and/or characterize an immune response of an individual against selected antigens, and optionally assess the kind of immune response (e.g., identification of early, mid, late, or chronic infection), as well as disease progression, efficacy of therapy, etc. Most typically, the plurality of antigens will include at least 2 to 10 antigens, but significantly higher amounts of antigens are also contemplated, including at least 25%, more typically at least 50%, even more typically at least 75%, and most typically at least 90% of the proteome of the pathogen. In further typical aspects of the inventive subject matter, contemplated arrays are most preferably processed in a microfluidic device. For example, an array of antigens in such devices may be printed on a membrane or other material (e.g., nitrocellulose-coated carrier of less than 1 $cm^2$ area) that is then placed in a microfluidic device having sample/reagent inlet and outlet ports. Depending on the specific configuration, signals may be acquired using optical methods (e.g. CCD chip, flat bed scanner, etc.), electrical methods (e.g., voltammetric or amperometric), or other methods well known in the art. Alternatively, visual detection or detection using a regular flat bed scanner at 1200 dpi resolution and/or fluorescence detection is also deemed suitable.

In another example, immunodominant antigens according to the inventive subject matter may also be employed to generate an antibody preparation that can be used as a passive vaccination for therapeutic treatment of a disease caused by the above pathogens.

In still further contemplated aspects, the immunodominant antigens presented herein may also be employed in the manufacture of a vaccine that comprises at least one, and more typically at least two of the immunodominant antigens encoded by nucleic acids according to SEQ ID NO:1 to SEQ ID NO:1150. More preferably, however, contemplated vaccines will include between two and five, or at least six, and even more antigens, of which at least one of the antigens is an immunodominant antigen. Such vaccine compositions may be directed to elicit immunity against single or multiple serotypes and may thus comprise distinct immunodominant antigens, optionally from multiple and distinct serotypes and/or species. Moreover, it should be appreciated that vaccines may be produced that predominantly, or even exclusively, comprise immunodominant antigens of a single parameter. For example, a vaccine may comprise immunodominant antigens that are characteristic for a population that has recovered from an infection with the pathogen without drug intervention. In less preferred aspects, the sequences according to SEQ ID NO:1 to SEQ ID NO:1150 may also be employed as DNA vaccines, or be part of an in vivo expression system that triggers an immune response against the in vivo produced recombinant antigen or fragment thereof.

With respect to suitable formulations of vaccines, it should be recognized that all known manners of producing such vaccines are deemed appropriate for use herein, and a person of ordinary skill in the art will be readily able to produce such vaccines without undue experimentation (see e.g., "Vaccine Adjuvants and Delivery Systems" by Manmohan Singh; Wiley-Interscience (Jun. 29, 2007), ISBN: 0471739073; or "Vaccine Protocols" (Methods in Molecular Medicine) by Andrew Robinson, Martin P. Cranage, and Michael J. Hudson; Humana Press; 2 edition (Aug. 27, 2003); ISBN: 1588291405). Therefore, suitable vaccines may be formulated as injectable solutions, or suspensions, intranasal formulations, or as oral formulations.

Examples

The following examples are provided for *Plasmodium falciparum* (Pf) and, in part, also for *Vaccinia virus* as target organism. Substantially similar protocols were adapted to identify immunodominant antigens from *Burkholderia pseudomallei, Borrelia burgdorferi, Brucella melitensis, Chlamydia muridarum, Coxiella burnetii, Francisella tulare*, Herpes virus 1 and 2, and *Mycobacterium tuberculosis*.

Genes/ORFs for Pf were selected in silico and associated (where known) with various specific criteria, including pattern of stage-specific gene or protein expression deduced from genomic, proteomic, or cell biology datasets. PCR primers were then computed to allow for amplification, cloning, and expression as further outlined below. So selected genes/ORFs were then amplified cloned using a high throughput PCR cloning method as previously described by the inventors (Genome Res 14, 2076-2082 (2004)). Efficiencies of the overall process of PCR amplification and cloning were typically about 90% (with higher values for smaller genes and lower values for larger [>2 kBp] genes). A subset of the amplified and cloned genes were sequenced to confirm the identity of the target gene and to verify that mutations were not introduced as a result of the amplification and cloning process. On average, 97% sequence identity was noted.

As compared with other organisms, Pf proteins have often been difficult to express by conventional methodologies in bacterial, yeast or insect expression systems. The inventors therefore evaluated the efficiency of Pf protein expression in an *E. coli* based cell-free in vitro transcription/translation system (RTS100, commercially available from Roche Biosciences) using 295 different cloned and HIS-tagged Pf ORFs as templates. Quantification of the signal intensities revealed that 94% of signals were ≥4× the controls. A replicate HA-tagged Pf array was produced with two sets of Pf vectors, containing a stop codon either before or after the HA tag. Such tagged recombinant proteins allow facile identification, rough quantification, and purification where desired. Uniformly high expression efficiencies >90% were obtained in all cases. Remarkably, the amount of protein printed per chip is essentially at saturation (data not presented), meaning that differences between any detected antigen reactivities would not be due to differences in the amount of protein spotted.

PCR amplified and cloned genes/ORFs were expressed in the RTS100 cell-free in vitro transcription/translation system, and printed in duplicate onto microarray chips. These chips were probed with sera from a population of subjects (n=12) who were naturally exposed to malaria in a hyperendemic region of Kenya, a population of subjects (n=10) who were experimentally immunized with radiation attenuated Pf sporozoites and either protected (n=6) or not protected (n=4) against challenge with infectious sporozoites, or a population of malaria-naïve individuals.

Most notably, sera from malaria exposed individuals and sporozoite immunized subjects reacted against different subsets of expressed proteins. For the naturally exposed group, there were 156 antigens with p values <1e−3 and 77 antigens with p values <1e−7 while for the pre-challenge sera from the irradiated sporozoite immunized groups, there were 17 antigens with p values <1e−3 in the protected group and nine antigens in the unprotected group. The low p values indicate that the signals obtained from the chip are highly significant. Background reactivity from naïve donors was low (data not presented).

A similar panel was prepared for *vaccinia virus* with primary and secondary exposure and with a variola as a control group. The results of this series of experiments can be taken from the summary panel of FIG. 1, in which the different populations provided different targets for different types of antibodies. Here, a proteome-wide view is provided for the serological response to DryVax *vaccinia* and smallpox. Protein microarrays displaying 210 different *vaccinia* strain WR proteins were probed with sera from individuals before, and 28-30 days after, primary or secondary vaccination with DryVax. All signal intensities have been background subtracted of control spots that lack template DNA, and assigned a color, with the dark end of the spectrum representing the highest signals. At the low end of the scale, a signal intensity of 5000 has been used as the cut-off above which a response was considered positive. Thus all negative responses are light. No significant reactivity was seen with any of the secondary antibodies alone (not shown). The combined IgG, IgM and IgA profiles in primary and secondary DryVax infections include 64 and 49 different antigens (~29% and ~22% of the proteome), respectively. Interestingly, most antigens are recognized by fewer than half the vaccinees, and late antigens dominate both primary and secondary responses. Despite variola being a different orthopox species, antibody profiles of individuals infected with smallpox are essentially indistinguishable from DryVax or VIG profiles.

Figure 2:
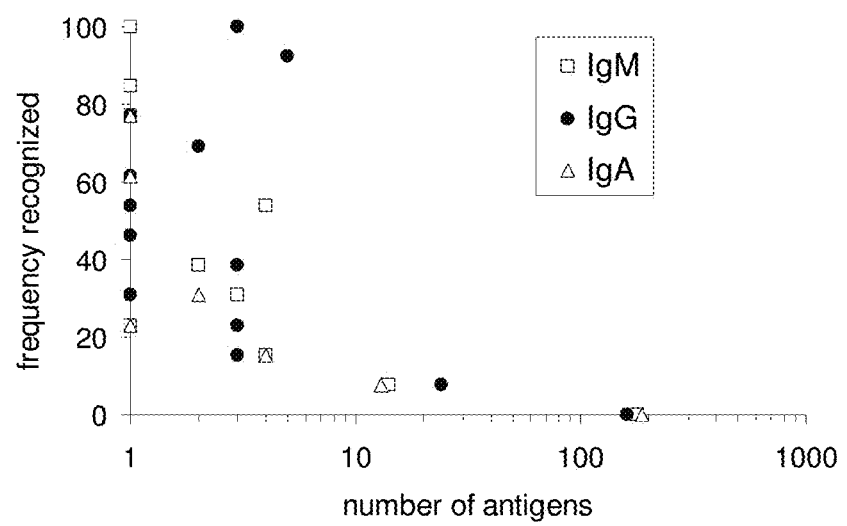
FIG. 2 is a graph illustrating the relative scarcity of antigen recognition of selected antibody types.
Figure 3A:
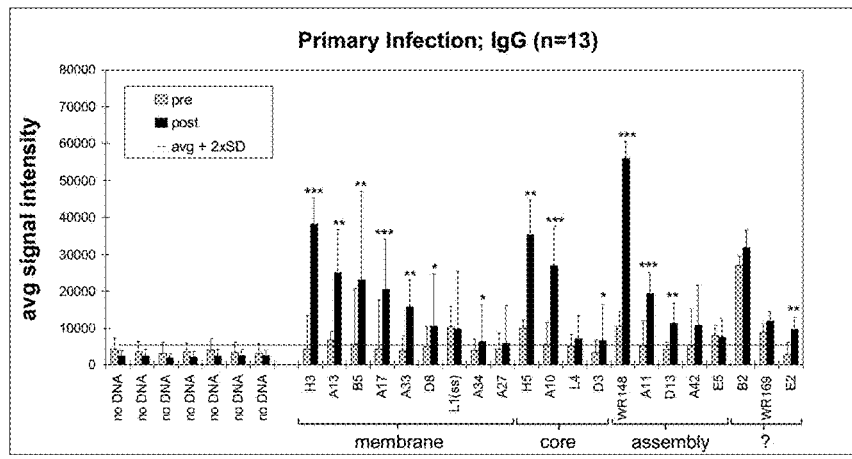
FIGS. 3A and 3B are exemplary graphs depicting the average signal intensities of a plurality of immune responses against various antigens of primary (A) and secondary (B) infections.
Figure 3B:
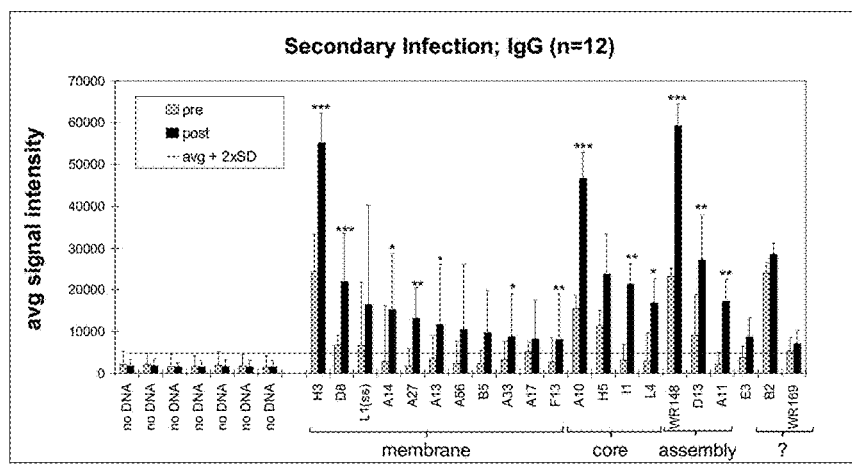

As can be taken from FIG. 2, the antibody profiles between individuals responding to the DryVax are heterogeneous to a significant degree. Each protein in the proteome was scored seropositive if its signal intensity was >5000 after subtraction of its signal intensity seen with pre-immune serum. As is readily apparent, there were relatively few antigens that were frequently recognized. Indeed, most positive antigens were recognized by fewer than half the vaccinees, reflecting the heterogeneity of individual profiles, and with that reflecting the difficulty in traditional vaccine development to obtain a vaccine that is effective for a large fraction of a population. FIGS. 3A and 3B depict immunodominance profiles of *vaccinia* antigens in human primary and secondary responses. Average signal intensities from sera 28-30 days post vaccination, with corresponding pre-vaccination signals, were plotted as raw data. Primary responses are shown in panel (A) and secondary responses are in panel (B). In each panel, a cut-off, indicated by the horizontal line, was set by the average of 7 pairs of control spots (expression reactions lacking DNA template) plus 2 standard deviations. The relatively large standard deviations are due to the inter-individual heterogeneity. Pre and post responses to an antigen that are significantly different by 2-tailed, paired t-test are indicated as * p<0.0005,  p<0.005, * p<0.05. Others were considered non-significant.

Characteristic profiles of antigen reactivity were noted for each of the clinically distinct cohorts, indicating that immunoreactive antigens identified in this way may be useful for serodiagnostic tests that are not only relevant with respect to the observed reactivity, but also with respect to a disease parameter (e.g., previous exposure to the pathogen, duration of exposure to the pathogen, chronic infection, at least partial immunity to infection with the pathogen, expected positive outcome upon treatment, etc.). Remarkably, and with regard to the Pf immune panel, the naturally exposed cohort who was protected against clinical disease, but not Pf parasitemia, gave an entirely different immunoreactivity profile compared with the sporozoite-vaccinated cohort that has both anti-disease and anti-parasite immunity. Further, naturally exposed subjects reacted more strongly to a larger number of antigens than the sporozoite immunized subjects, and the subset of sporozoite vaccinees that were protected reacted more strongly to a larger number of antigens than the unprotected group. Still further, the antigen repertoire in the sporozoite immunized and protected group immediately prior to challenge was unchanged after challenge. In contrast, immunized volunteers who developed clinical malaria following experimental challenged (experimentally infected) developed an additional subset of antibodies after challenge; many were similar to the naturally exposed profile but some were unique to the experimentally infected group.

In addition to the subset of antigens identified on the basis of intensity of response, a subset of antigens which were less immunoreactive but nonetheless frequently recognized was identified. For example, for naturally Pf exposed subjects, 121 antigens were recognized at p<0.05 and frequency ≥50% regardless of signal intensity; 20 antigens were recognized by 12/12 subjects (11/20 at signal intensities <4.0). For irradiated sporozoite immunized subjects 82 antigens were recognized pre-challenge at p<0.05 and frequency ≥50% by both protected and unprotected subjects; five antigens were recognized by 10/10 subjects (2/5 at signal intensities <4.0). It is therefore contemplated that antigens recognized in high frequency but not necessarily at high magnitude may represent good diagnostic targets.

Figure 4A:
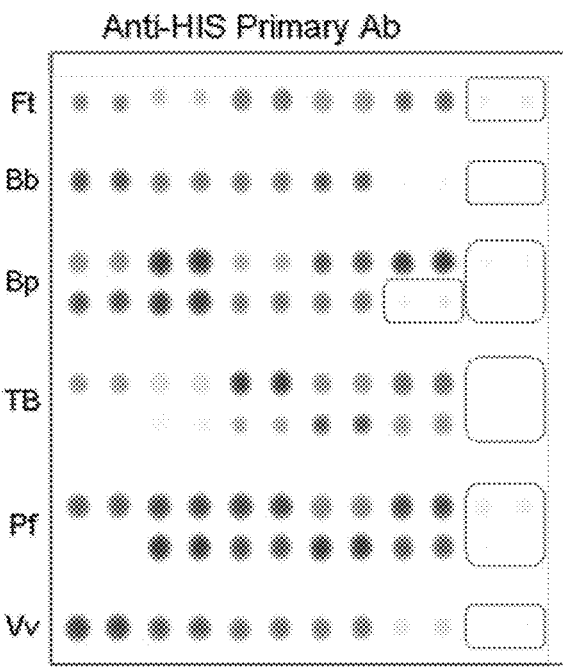
FIGS. 4A and 4B are exemplary scans of diagnostic arrays comprising multiple immunodominant antigens of multiple distinct pathogens depicting approximate quantities of antigens deposited (A) and their reaction against human serum of a patient infected with a pathogen.
Figure 4B:
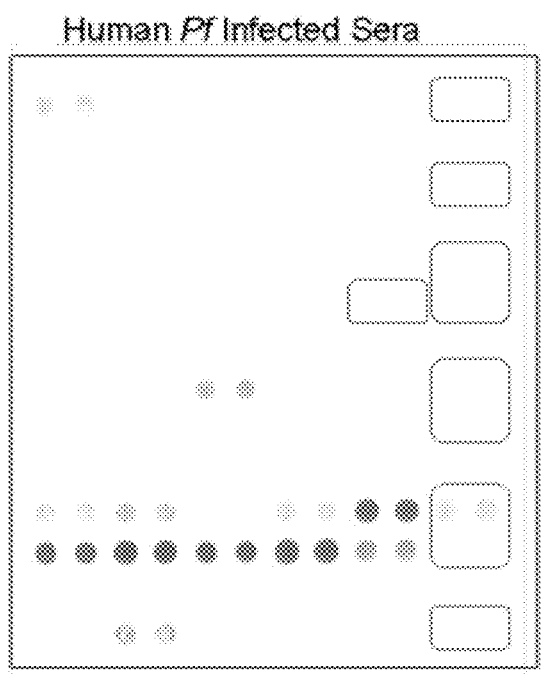

To illustrate how immunodominant antigen sets identified in this way can be used for serodiagnostics, a protein microarray containing immunodominant antigens from several infectious agents was fabricated. The antigens were expressed in the cell-free in vitro transcription/translation system, printed onto FAST slides without further purification, and probed with anti-histidine primary antibody followed by alkaline phosphatase conjugated secondary antibody. The slide was developed with alkaline phosphatase substrate and scanned using an ordinary desktop document scanner. The result of this scan is illustrated in FIG. 4A depicting the 'antigen-loading' of the array. Immunodominant antigens represented on this 'diagnostic chip' are derived from: *F. tularensis* (Ft), *B. pseudomallei* (Bp), *B. burgdorferi* (Bb), *M. tuberculosis* (TB), *P. falciparum* (Pf) and *vaccinia virus* (Vv). The negative control spots (within circles) correspond to in vitro expression reactions without plasmid template. An example of the same slide probed with serum from one of the Kenyan subjects naturally exposed to Pf is shown in FIG. 4B. The strongest signals were against the Pf immunodominant antigen set, with weak reactivity toward *vaccinia virus* and *M. tuberculosis* antigens. Reactivity against non-Pf antigens could be a consequence of prior exposure to these infectious agents or to cross-reactivity.

The following exemplary protocol is provided to illustrate the steps and reagents used in the identification of the immunodominant antigens of Pf presented herein. Unless expressly stated, standard laboratory techniques well known to a person of ordinary skill in the art were employed.

PCR Amplification of Linear Acceptor Vector

Plasmid pXT7 (10 µg; 3.2 kb, KanR) was linearized with BamHI (0.1 µg/µl DNA/0.1 mg/ml BSA/0.2 units/µl BamHI; 37° C. for 4 hr; additional BamHI was added to 0.4 units/µl at 37° C. overnight). The digest was purified using a PCR purification kit (Qiagen, Valencia, Calif.), quantified by fluorometry using Picogreen (Molecular Probes, Carlsbad, Calif.) according to the manufacturer's instructions, and verified by agarose gel electrophoresis (1 µg). One ng of this material was used to generate the linear acceptor vector in a 50 µl PCR using 0.5 µM each of primers 5'-CTACCCAT-ACGATGTTCCGGATTAC (SEQ ID NO:1151) and 5'-CTCGAGCATATGCTTGTCGTCGTCG (SEQ ID NO:1152), and 0.02 units/µl Taq DNA polymerase (Fisher Scientific, buffer A)/0.1 mg/ml gelatin (Porcine, Bloom 300; Sigma, G-1890)/0.2 mM each dNTP with the following conditions: initial denaturation of 95° C. for 5 min; 30 cycles of 95° C. for 0.5 min, 50° C. for 0.5 min, and 72° C. for 3.5 min; and a final extension of 72° C. for 10 min.

PCR Amplification of ORF Insert

A total of 1-10 ng of Pf genomic DNA (3D7 strain) was used as template in a 50-µl PCR. The following primers were used (0.5 µM each): 5'-CATATCGACGACGACGA-CAAGCATATGCTCGAG (SEQ ID NO:1153; 20-mer ORF specific at the 5' end) and 5'-ATCTTAAGCGTAATCCG-GAACATCGTATGGGTA (SEQ ID NO:1154; 20-mer ORF specific at the 3' end). The Pf genome is the most A+T rich genome sequenced to date with an overall (A+T) composition of 80.6%, rising to ~90% in introns and intergenic regions. Consequently, PCR amplification of Pf genes using genomic DNA template was problematic. Initially, PCR was carried out using regular Taq DNA polymerase: 0.02 units/µl TaqDNA polymerase (buffer A, Fisher Scientific)/0.1 mg/ml gelatin (Bloom 300, Porcine; G-1890, Sigma)/0.2 mM each dNTP. Conditions were as follows: initial denaturation of 95° C. for 5 min; 30 cycles of 20 sec at 95° C., 30 sec at 50° C., and 60 sec/kb at 72° C. (1-3 min on average, based on ORF size); and a final extension of 72° C. for 10 min. PCR products that were more difficult to produce were reamplified by using a 30 sec annealing time at 45° C. or 40° C., instead of 30 sec at 50° C. Also, the extension temperature was decreased from 65-72° C. to 50° C. Subsequently PCR products were obtained using a Taq polymerase with improved proof-reading characteristics (Triplemaster from Eppendorf), increasing the efficiency of the PCR step to 87%: 0.04 units/µl Triple Master PCR system (high-fidelity buffer, Eppendorf)/0.4 mM each dNTP (Eppendorf). Conditions were as follows: initial denaturation of 95° C. for 3 min; 35 cycles of 15 sec at 95° C., 30 sec at 40° C., and 60 sec/kb at 50° C. (1-3 min on average, based on ORF size); and a final extension of 50° C. for 10 min., PCR products that were difficult were reamplified using 50 ng genomic DNA. The PCR product was visualized by agarose gel electrophoresis (3 µl). For quantification, the product was purified (PCR purification kit, Qiagen) and quantified by fluorometry. Since the reliability of producing the desired PCR product decreases as the length of the genomic DNA fragment increases, exons longer than 3,000 by were divided into multiple overlapping sections, with 50 nucleotide overlaps.

In Vivo Recombination Cloning

Competent cells were prepared in our laboratory by growing DH5α cells at 18° C. in 500 ml of SOB (super optimal broth) medium (2% tryptone/0.5% yeast extract/10 mM NaCl/2.5 mM KCl/20 mM $MgSO_4$) to an OD of 0.5-0.7. The cells were washed and suspended in 10 ml of pre-chilled PCKMS buffer (10 mM Pipes/15 mM $CaCl_2$/250 mM KCl/55 mM $MnCl_2$/5% sucrose, pH 6.7) on ice, and 735 µl of DMSO was added dropwise with constant swirling. The competent cells were frozen on dry ice-ethanol in 100-µl aliquots and stored at −80° C. Each transformation consisted of the following: 10 µl of competent DH5α a and 10 µl of DNA mixture (40 ng of PCR-generated linear vector/10 ng of PCR-generated ORF fragment; molar ratio, 1:1; vector, 1-kb ORF fragment). For transformation, the purification of PCR product was unnecessary. The mixture was incubated on ice for 45 min, heat shocked at 42° C. for 1 min, and chilled on ice for 1 min; mixed with 250 µl of SOC (super optimal catabolizer) medium (2% tryptone/ 0.55% yeast extract/10 mM NaCl/10 mM KCl/10 mM $MgCl_2$/10 mM $MgSO_4$/20 mM glucose); incubated at 37° C. for 1 hr; diluted into 3 ml of LB medium supplemented with 50 µg of kanamycin per ml (LB Kan 50); and incubated with shaking overnight. The plasmid was isolated and purified from this culture, without colony selection.

In Vitro Protein Expression

Plasmid templates used for in vitro transcription/translation were prepared by using QIAprep Spin Miniprep kits (Qiagen), including the "optional" step, which contains protein denaturants to deplete RNase activity. In vitro transcription/translation reactions (RTS 100 *Escherichia coli* HY kits; Roche) were set up in 25 µl PCR 12-well strip tubes and incubated for 5 h at 30° C., according to the manufacturer's instructions.

Immuno-Dot Blots

To assess relative efficiency of protein expression, 0.3 µl of whole rapid-translation system (RTS) reactions were spotted manually onto nitrocellulose and allowed to air dry before blocking in 5% nonfat milk powder in TBS containing 0.05% Tween 20. Blots were probed with hyperimmune sera diluted to 1:1,000 in blocking buffer with or without 10% *E. coli* lysate. Routinely, dot blots were stained with both mouse anti-poly-HIS mAb (clone, HIS-1; H-1029, Sigma) and rat anti-hemagglutinin (HA) mAb (clone, 3F10; 1 867 423, Roche), followed by alkaline phosphatase-conjugated goat anti-mouse IgG (H+L) (BioRad) or goat anti-rat IgG (H+L) (Jackson ImmunoResearch) secondary Abs, respectively. Bound human Abs were visualized with nitroblue tetrazolium (nitro-BT) developer to confirm the presence of recombinant protein.

Microarray Chip Printing

For microarrays, 10 µl of 0.125% Tween 20 was mixed with 15 µl of RTS reaction (to a final concentration of 0.05% Tween 20), and 15-µl volumes were transferred to 384-well plates. The plates were centrifuged at 1,600×g to pellet any precipitate, and supernatant was printed without further purification onto nitrocellulose-coated FAST glass slides (Schleicher & Schuell) by using an OmniGrid 100 microarray printer (Genomic Solutions, Ann Arbor, Mich.). All ORFs were spotted in duplicate to enable statistical analysis of the data. Data values reported herein represent the average of pairs. In addition, each chip contained an area printed with controls consisting of RTS reaction using no DNA.

Protein Microarray Screening

Microarray chips were probed with human serum that was first pre-absorbed against E. coli-lysate to block anti-E. coli antibodies as described previously. In the absence of pre-absorbing, high titers of anti-E. coli antibodies could mask any antigen-specific responses when using whole RTS reactions on dot blots and arrays. For all staining, slides were first blocked for 30 min in protein array-blocking buffer (Schleicher & Schuell) and then incubated in serum for 2 hr, at room temperature. Antibodies were visualized with Cy3-conjugated secondary Abs (biotinylated secondary followed by Streptavidin PBXL-3, for HIS-probing) (Jackson ImmunoResearch) and scanned in a ScanArray 4000 laser confocal scanner (GSI Lumonics, Billerica, Mass.). Fluorescence intensities were quantified by using QuantArray software (GSI Lumonics). Other studies in our affiliated University laboratory have established that the results from scanned microarray chips can be represented numerically and that signal intensity is proportional to antibody titer (data not shown).

ELISA

To validate the immunoreactivity detected by the protein microarrays, sera was analyzed by ELISA against a panel of known and well-characterized Pf pre-erythrocytic stage antigens (PfCSP, PfLSA1, and PfExp1) and erythrocytic stage antigens (PfAMA1, PfMSP1), as previously described. The mean OD readings of quadruplicate assays were recorded, and results reported as the OD value at each serum dilution and as endpoint dilution (defined as greater than the mean+/−3 standard deviation of negative control sera).

Indirect Fluorescent Antibody Test (IFAT)

Antibody recognition of Pf (NF54/3D7) sporozoite or blood stage parasites was evaluated by IFAT as described previously. Reactivity was scored as positive when the immunofluorescence pattern of the parasite was recognized and when the fluorescence was above the background of the negative controls. IFAT results were expressed as the endpoint serum dilution at which positive fluorescence was detected.

Malaria-Exposed Study Populations

Individuals were selected for study on the basis of malaria history. Studies were conducted in compliance with all applicable Federal regulations governing the protection of human subjects. The irradiated sporozoite study protocol was approved by the Naval Medical Research Center Committee for the Protection of Human Subjects, the Office of the Special Assistant for Human Subject Protections at the Naval Bureau of Medicine and Surgery, and the Human Subjects Research Review Board of the Army Surgeon General. The Kenyan samples were collected under a study protocol approved by the Naval Medical Research Institute's Committee for the Protection of Human Subjects, the Walter Reed Army Institute of Research Human Use Committee, and the Kenya Medical Research Institute/National Ethical Review Committee. Written informed consent was obtained from all subjects.

Sporozoite Immunized Volunteers

Caucasian volunteers (n=10) were experimentally immunized with radiation-attenuated Pf sporozoites as previously described (The Journal of Infectious Diseases (2002), Vol: 185, p 1155-64). Subjects were challenged by the bites of 5 infected Anopheline mosquitoes, and evaluated for the development of clinical malaria. Protection was defined as complete absence of blood-stage parasitemia (sterile protection). Six of the 10 immunized volunteers were protected against sporozoite challenge and were classified as sporozoite-immune; four were not protected and were classified as sporozoite-exposed but non-immune. Serum samples were collected from each volunteer prior to immunization (pre-bleed), at the completion of the immunization series and immediately prior to challenge (pre-challenge), and following challenge (post-challenge). Pre- and post-challenge IFAT titers against Pf sporozoites were 613.3 (mean; range 160-1280) and 170 (mean; range 40-320) for protected and unprotected volunteers, respectively.

Individuals Naturally Exposed to Malaria

Kenyan subjects (n=12) were residents of the Asembo Bay area of Kenya. In this area, the year round prevalence of Pf infection amongst children 6 months to 6 years of age has been documented as 94.4-97.8%. Enrolled subjects reported an average of 2.1 episodes of clinical malaria within the previous year. The study cohort derives from a subset of 185 volunteers previously enrolled in an immunoepidemiology study and selected for the current study on the basis of sex, age, malaria history and recognition of native Pf sporozoites and parasitized erythrocytes, by IFAT. Pf sporozoite and blood-stage IFAT titers for the pool of hyperimmune sera from these 185 individuals were 5,120 and 81,920, respectively.

Analysis of Individual Array Measurements

As a first step in determining significantly bound antigens for each serum/array using statistical tests, the inventors defined the true negative control signal to compare each antigen with the mean signal of all spotted controls on the array. Since comparisons needed to be carried across arrays, the inventors transformed the raw signals using the vsn (asinh transformation, similar to log for higher intensities) method, shown to effectively calibrate array measurements through shifting and scaling and also to stabilize the variance in DNA microarray and 2D difference gel electrophoresis data analyses. Because standard deviation (SD) estimates can be unreliable (artificially high or low) when there is low replication of measurements, and since each antigen was spotted only twice per array, the inventors applied the Bayes-regularization technique described in Baldi and Long (Bioinformatics (2001), 17, 509-519; Baldi, P. and Hatfield, G. W. (2002) DNA Microarrays and Gene Expression: From Experiments to Data Analysis and Modeling, Cambridge University Press, Cambridge, UK; and Bioinformatics (2006), Vol. 22, No. 14; p: 1760-1766, all incorporated by reference herein). This technique derives more robust estimates (as shown in the context of DNA microarray data analysis) of the SD of each antigen as a weighted combination of the sample SD and the pooled SD of neighboring antigens with similar signal intensity. Using these new regularized estimates for the standard deviation, we conducted a series of Bayes-regularized one-sided t-tests on antigens with higher mean signal than the defined control to reliably estimate the signal changes between each antigen and control, and computed the corresponding p-values.

Analysis of Groups of Array Measurements

In addition to determining the positive antigens recognized by each of the individual sera, the inventors averaged replicated spot measurements per sera and pooled the responses for each cohort/group, to identify the positive antigens while taking into account the biological variation within the sera in each group. Since the measurements were obtained from different arrays, the inventors performed a calibration and variance stabilization of the measurements using the vsn method (Bioinformatics 18 Suppl 1, S96-104 (2002) prior to the pooling of measurements. As for the analysis of individual sera, the inventors defined the true negative control using the mean control signal spotted on the arrays. One-sided Bayes-regularized t-tests were performed within each group to compare and rank the antigens with a higher mean signal than the control. For the individual and cohort/group analysis, using the average SD of 5-30 neighboring antigens along with a weight of 5 "pseudocounts" for computing the Bayes-regularized SD was observed to achieve a moderate regularization effect. Given the large number of hypotheses being tested, the inventors applied the method in Storey and Allison et. al. to the set of p-values to estimate the experiment-wide false discovery rates (FDR). For the individual and cohort analyses of the 43 arrays, a p-value cutoff of 0.05 corresponded to an FDR level of 0.06-0.065. With the additional criteria applied for determining a positive response as described below, the inventors expect the FDR to be lower.

Analysis of Frequency of Response

In addition to analyzing the intensity of response (as described above), the inventors also assessed the frequency of response for each antigen as the number of individuals within a given cohort for which that antigen was positive on the basis of normalized signal intensity relative to control.

Criteria of Positivity (Immunodominance)

Final classification of antigen reactivity was made taking into account both magnitude of response (signal intensity) and frequency of recognition. The responses by a particular cohort of donors were considered positive overall if all of the following criteria were met: (1) normalized signal intensity >4.0 (ratio of signal intensity of test relative to control >4.0); (2) response was statistically significant ($p<0.05$) compared with control signal intensity; and (3) frequency of positive responses within a particular cohort ≥2.0.

Thus, specific embodiments and applications of immunodominant compositions and methods have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Furthermore, where a definition or use of a term in a reference, which is incorporated by reference herein is inconsistent or contrary to the definition of that term provided herein, the definition of that term provided herein applies and the definition of that term in the reference does not apply.

Sequence Listing

The Sequence Listing providing sequences with the SEQ ID NO:1 to SEQ ID NO:1150 is submitted as a single file on a single compact disc in computer readable format (CRF; three copies of the disc were submitted together with the original CRF disc), wherein the single file is entitled "101519.0001PCT_Sequence_Listing_ST25.txt", which was created Oct. 25, 2007, which has a size of 1908 kb, and which is incorporated by reference herein. Therefore, four identical discs, each containing a single sequence listing file with the file name "101519.0001PCT_Sequence_Listing_ST25.txt" have been submitted.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10174311B2). An electronic copy of the "Sequence Listing" will also be available from the USPTO upon request and payment of the fee set forth in 37 CFR 1.19(b)(3).

What is claimed is:

1. A method comprising: preparing unpurified mixed amplicons having different nucleotide sequences in a polymerase chain reaction using pairs of primers, each pair of primers suitable to generate amplicons of a single open reading frame by amplifying at least a portion of the single open reading frame;
   generating a plurality of recombinant cells comprising recombinant plasmids by directly transforming a plurality of cells with the unpurified mixed amplicons and linear vectors such that the recombinant plasmids are generated by in vivo recombination cloning;
   isolating the recombinant plasmids from the recombinant cells without colony selection;
   generating a mixture of cloned antigens by directly using the isolated recombinant plasmids in in vitro transcription and in vitro translation;
   and placing the mixture of cloned antigens onto a solid carrier without purification;
   wherein amounts of the mixture of cloned antigens placed on the solid carrier are essentially at saturation.

2. The method of claim 1, further comprising:
   determining a single open reading frame in a part of a pathogen's genome; and
   determining a pair of primers suitable to generate amplicons of the single open reading frame, or a portion thereof.

3. The method of claim 2, further comprising:
   determining a plurality of splice mutations in the single open reading frame; and
   determining one or more pairs of primers suitable to generate amplicons of the splice mutations in the single open reading frame, or a portion thereof.

4. The method of claim 1, wherein the recombinant plasmids encoding the mixture of cloned antigens are polyclonally multiplied.

5. The method of claim 1, wherein the mixture of cloned antigens is placed onto the solid carrier in an array.

6. A method of detecting antibodies directed against antigens of a pathogen in an antibody-containing bodily fluid sample comprising:
   preparing unpurified mixed amplicons having different nucleotide sequences in a polymerase chain reaction using pairs of primers, each pair of primers suitable to generate amplicons of a single open reading frame by amplifying at least a portion of the single open reading frame;
   generating a plurality of recombinant cells comprising recombinant plasmids by directly transforming a plurality of cells with the unpurified mixed amplicons and linear vectors such that the recombinant plasmids are generated by in vivo recombination cloning;
   isolating the recombinant plasmids from the recombinant cells without colony selection;
   generating a mixture of cloned antigens by directly using the isolated recombinant plasmids in in vitro transcription and in vitro translation;
   placing the mixture of cloned antigens onto a solid carrier without purification;
   wherein amounts of the mixture of cloned antigens placed on the solid carrier are essentially at saturation;
   and contacting the sample with the mixed cloned antigens on the solid carrier and detecting antibodies in the sample which bind to the mixed cloned antigens on the solid carrier.

7. The method of claim 6, further comprising:
   determining a single open reading frame in a part of the pathogen's genome; and
   determining a pair of primers suitable to generate amplicons of the single open reading frame, or a portion thereof.

8. The method of claim 7, further comprising:
   determining a plurality of splice mutations in the single open reading frame; and
   determining one or more pairs of primers suitable to generate amplicons of the splice mutations in the single open reading frame, or a portion thereof.

9. The method of claim 6, wherein the bodily fluid is derived from a person previously exposed to the pathogen.

10. The method of claim 6, wherein the recombinant plasmids encoding the mixture of cloned antigens are polyclonally multiplied.

11. The method of claim 6, wherein the mixture of cloned antigens is placed onto the solid carrier in an array.

12. A method comprising the steps of preparing a plurality of amplicons having different nucleotide sequences in a polymerase chain reaction, generating a plurality of recombinant plasmids comprising the plurality of amplicons by transforming cells by in vivo recombination cloning, isolating the recombinant plasmids, and generating cloned antigens by in vitro transcription of and in vitro translation using the recombinant plasmids, the improvement comprising:
   (a) directly transforming cells with a linear vector and a mixture of the plurality of amplicons, wherein the amplicons are unpurified, to produce a plurality of recombinant plasmids;
   (b) isolating the plurality of recombinant plasmids from the transformed cells without colony selection;
   (c) directly using the isolated recombinant plasmids in in vitro transcription and in vitro translation to generate a mixture of cloned antigens;
   (d) placing the mixture of cloned antigens onto a solid carrier without purification, wherein amounts of the mixture of cloned antigens placed on the solid carrier are essentially at saturation.

13. The method of claim 12, wherein the recombinant plasmids encoding the mixture of cloned antigens are polyclonally multiplied.

14. The method of claim 12, wherein the mixture of cloned antigen is placed onto the solid carrier in an array.

* * * * *